(12) United States Patent
Fischer et al.

(10) Patent No.: US 10,150,746 B2
(45) Date of Patent: Dec. 11, 2018

(54) PREPARATION OF PANTOLACTONE

(71) Applicant: BASF SE, Ludwigshafen am Rhein (DE)

(72) Inventors: Klaus Fischer, Neustadt (DE); Benjamin Nehls, Mannheim (DE); Jürgen Deschler, Elmstein (DE); Walter Dobler, Schwetzingen (DE); Arnulf Lauterbach, Ludwigshafen (DE); Sabine Schlautmann, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/737,551

(22) PCT Filed: Jun. 17, 2016

(86) PCT No.: PCT/EP2016/063978
§ 371 (c)(1),
(2) Date: Dec. 18, 2017

(87) PCT Pub. No.: WO2016/202965
PCT Pub. Date: Dec. 22, 2016

(65) Prior Publication Data
US 2018/0111911 A1    Apr. 26, 2018

(30) Foreign Application Priority Data
Jun. 19, 2015 (EP) .................................. 15172900

(51) Int. Cl.
C07D 307/33 (2006.01)
C07B 63/04 (2006.01)
C07B 55/00 (2006.01)
C07B 41/06 (2006.01)

(52) U.S. Cl.
CPC .......... *C07D 307/33* (2013.01); *C07B 41/06* (2013.01); *C07B 55/00* (2013.01); *C07B 63/04* (2013.01)

(58) Field of Classification Search
CPC .................................................. C07D 307/33
USPC ....................................................... 549/319
See application file for complete search history.

(56) References Cited

U.S. PATENT DOCUMENTS

| 2,328,000 | A |   | 8/1943  | Finkelstein |
|-----------|---|---|---------|-------------|
| 4,082,775 | A | * | 4/1978  | Couderc ............. C07D 307/33 |
|           |   |   |         | 549/319 |
| 4,200,582 | A |   | 4/1980  | Distler et al. |
| 6,998,258 | B1|   | 2/2006  | Kesseler et al. |

FOREIGN PATENT DOCUMENTS

| DE | 2627940 A1   |   | 2/1977  |              |
|----|--------------|---|---------|--------------|
| DE | 2758883 A1   |   | 7/1979  |              |
| EP | 0443406 A2   |   | 8/1991  |              |
| EP | 0528256 A1   |   | 2/1993  |              |
| FR | 1175516 A    |   | 3/1959  |              |
| GB | 597648 A     |   | 1/1948  |              |
| JP | 49038265     | * | 10/1974 | ........ C07D 307/33 |
| WO | WO-0132890 A1|   | 5/2001  |              |

OTHER PUBLICATIONS

International Preliminary Report on Patentability for International Application No. PCT/EP2016/063978, dated Dec. 21, 2017.
Effenberger, F., et al., "Enzyme Catalyzed Addition of Hydrocyanic Acid to Substituted Pivalaldehydes—A Novel Synthesis of (R)-Pantolactone", Tetrahedron: Asymmetry, vol. 6, No. 1, (1995), pp. 271-282.
Haughton, L., et al., "Enzymatic kinetic resolution of pantolactone: relevance to chiral auxiliary chemistry", Tetrahedron: Asymmetry, vol. 11, No. 8, (2000), pp. 1697-1701.
International Search Report for PCT/EP2016/063978 dated Aug. 2, 2016.
Rowicki, T., et al., "Calcium Pantothenate. Part 1. (R,S)-Pantolactone Technology Improvement at the Tonnage Scale", Industrial & Engineering Chemistry Research, vol. 45, No. 4, (2006), pp. 1259-1265.
Synoradzki, L., et al., "Calcium Pantothenate. Part 2. Optimisation of Oxynitrilase-Catalysed Asymmetric Hydrocyanation of 3-Hydroxy-2,2-dimethylaldehyde: Synthesis of (R)-Pantolactone", Organic Process Research & Development, vol. 10, No. 1, (2006), pp. 103-108.
Written Opinion of the International Searching Authority for PCT/EP2016/063978 dated Aug. 2, 2016.

\* cited by examiner

*Primary Examiner* — Nizal S Chandrakumar
(74) *Attorney, Agent, or Firm* — Drinker Biddle & Reath LLP

(57) ABSTRACT

The present invention relates to a novel process for the preparation of pantolactone by reaction of hydroxypivalaldehyde cyanohydrin in a phase separation process.

20 Claims, 1 Drawing Sheet

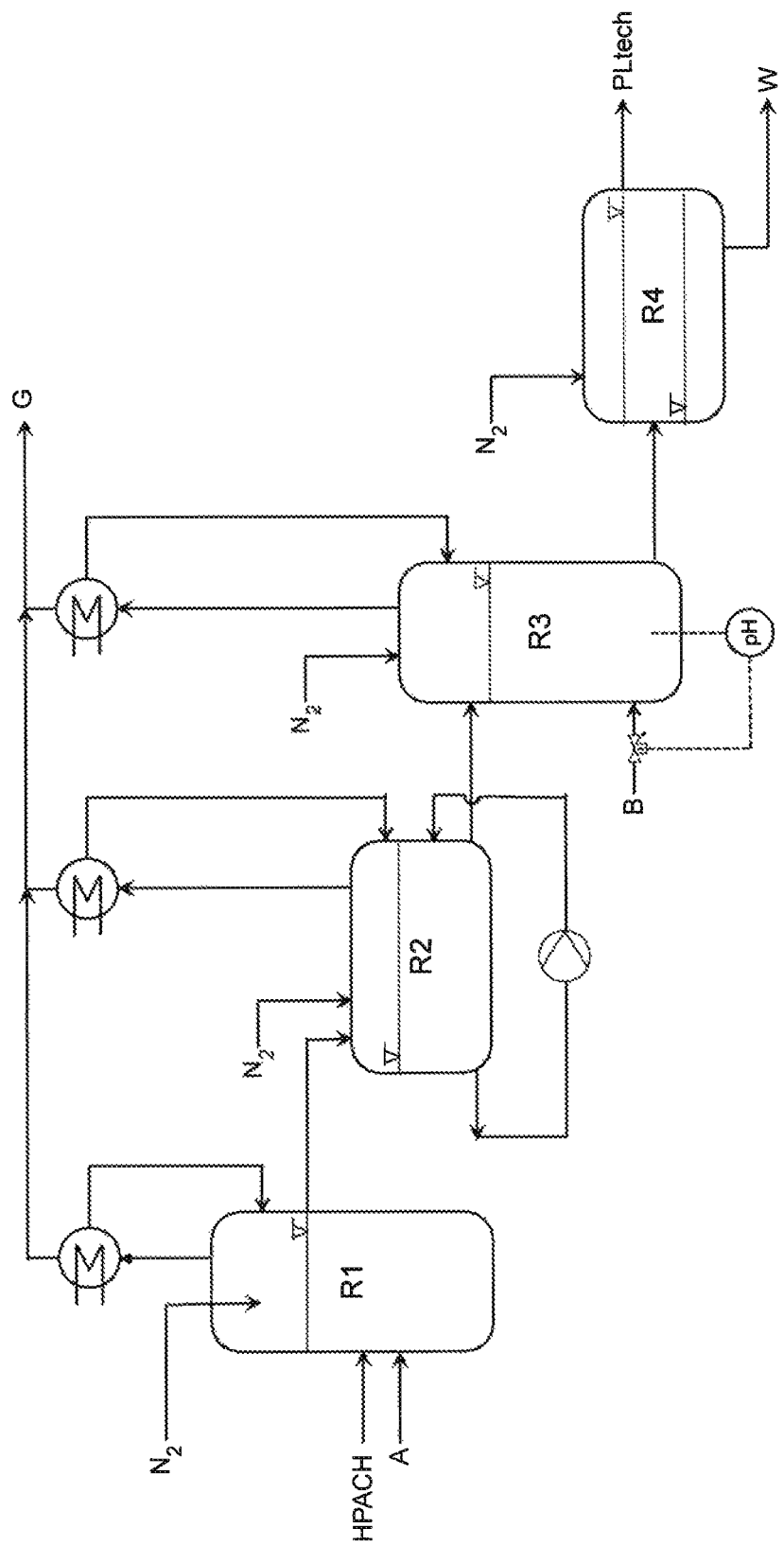

PREPARATION OF PANTOLACTONE

CROSS-REFERENCE TO RELATED APPLICATIONS

This application is a national stage application (under 35 U.S.C. § 371) of PCT/EP2016/063978, filed Jun. 17, 2016, which claims benefit of European Application No. 15172900.1, filed Jun. 19, 2015, both of which are incorporated herein by reference in their entirety.

BACKGROUND OF THE INVENTION

The present invention relates to a novel process for the preparation of pantolactone by reaction of hydroxypivalaldehyde cyanohydrin in a phase separation process.

PRIOR ART

Pantolactone (α-hydroxy-β,β-dimethyl-γ-butyrolactone, dihydro-3-hydroxy-4,4-dimethyl-2(3H)-furanone) is a valuable compound for producing cosmetic and pharmaceutical products. For example, D-pantolactone serves as a starting material for producing panthenol, also referred to as dexpanthenol or pantothenol. Panthenol has been used for a long time as an active ingredient for topical application for diseases of the skin and mucosa and cosmetically in skincare compositions. Pantothenic acid (vitamin $B_5$), the reaction product of pantolactone with β-alanine, is required for the synthesis of coenzyme A, which catalyzes the transfer of acyl groups in the metabolism. It is involved in the synthesis and degradation of carbohydrates, fats, amino acids and in the synthesis of cholesterol, which is used in the organism for the formation of steroid hormones.

It is known that formaldehyde can be reacted with isobutyraldehyde in an aldol addition to give hydroxypivalaldehyde (α,α-dimethyl-β-hydroxypropionaldehyde), and this aldehyde can then be further converted through addition of hydrocyanic acid to give hydroxypivalaldehyde cyanohydrin (2,4-dihydroxy-3,3-dimethylbutyronitrile) which serves as starting compound for producing pantolactone and/or the pantoates resulting from saponification of the pantolactone.

U.S. Pat. No. 2,328,000 describes the preparation of racemic pantolactone by reaction of formaldehyde and isobutyraldehyde in the presence of an alkali metal carbonate to give hydroxypivalaldehyde and then further by addition of hydrocyanic acid to give the cyanohydrin. The cyanohydrin is then reacted with concentrated HCl to give the lactone. In the process, in the only working example, an ethereal solution of the cyanohydrin is admixed with concentrated HCl, the mixture is left to stand overnight, during which ammonium chloride crystallizes out, following the addition of water, the ether is distilled off, the resulting mixture is adjusted to pH 7.2 with NaOH and then extracted continuously with ether. The pantolactone is isolated from the combined ether extracts.

FR 1 175 516 likewise describes a process for the preparation of pantolactone starting from formaldehyde and isobutyraldehyde by aldol reaction, formation of the cyanohydrin and its hydrolysis with ring closure. The pantolactone is isolated by extraction and purified by distillation.

DE-A-26 27 940 describes a process for the preparation of racemic pantolactone in which, in a first stage, hydroxypivalaldehyde is reacted with hydrocyanic acid prepared in situ and then, in a second stage, the cyanohydrin obtained in the process is hydrolyzed in a strongly acidic medium and the pantolactone formed is separated off and purified, wherein a) in both process stages the only solvent used is an alcohol having 5 or 6 carbon atoms, b) in the first stage the reaction of the hydroxypivalaldehyde with HCl and an alkali metal cyanide takes place at 10 to 20° C. and a pH of 8.2 to 9.2, with a 10% strength HCN excess being used, and c) in the second stage the acidic hydrolysis with excess concentrated HCl is carried out at a temperature of 100 to 105° C. over a period of 20 to 30 minutes and then the pantolactone is separated off.

DE-A-27 58 883 describes a process for the preparation of pantolactone, in which formaldehyde and isobutyraldehyde are reacted in the presence of 0.01 to 0.3 mol of tertiary amine per mole of isobutyraldehyde, the reaction mixture formed in this way is reacted with hydrocyanic acid, wherein the hydrocyanic acid concentration during the reaction is not more than 1% by weight, based on the reaction mixture, and the reaction mixture thus obtained is reacted with gaseous hydrogen chloride. To work up the end product, an extraction, e.g. with methylene chloride, and distillation of the solvent is described.

It is known, for the preparation of enantiomerically enriched pantolactone, to carry out the cyanohydrin synthesis enantioselectively. Thus, F. Effenberger et al. describe in Tetrahedron Asymmetry vol. 6, no. 1, pages 271-282, 1995, the enzymatically catalyzed addition of hydrocyanic acid onto substituted pivalaldehydes for the preparation of (R)-pantolactone.

L. Synoradzki et al. describe in Organic Research & Development 2006, 10, 103-108 an improved oxynitrilase-catalyzed asymmetric hydrocyanization of hydroxypivalaldehyde for the preparation of (R)-pantolactone. Here, an oxynitrilase from almond kernels, apple seeds and plum stones is used.

EP 0 528 256 A1 describes the enzymatic preparation of D-2,4-dihydroxy-3,3-dimethylbutyronitrile as chiral intermediate of D-pantolactone and D-pantothenic acid by reaction of hydroxypivalaldehyde with hydrogen cyanide in the presence of D-oxynitrilase. The reaction of the cyanohydrin to give pantolactone takes place in an aqueous-acidic medium at elevated temperature. Mineral acids, such as sulfuric acid or concentrated hydrochloric acid, are specified as suitable acids. To isolate the pantolactone, the reaction mixture is extracted with an organic solvent.

The known processes for the preparation of pantolactone have various disadvantages. For example, processes in which an aqueous pantoate solution with a low product-of-value concentration (often below 30%) is obtained as end product are limited as regards attainable production capacity. Moreover, a concentration of aqueous product solutions is always very costly in terms of energy. Processes according to which the pantolactone is isolated by extraction with an organic solvent require measures for the purification and reuse of the solvent. The use of hydrogen chloride and specifically of gaseous HCl for the conversion of the cyanohydrin to the pantolactone is not unproblematic on account of the high corrosivity. If then NaOH is used for the neutralization, the resulting products will generally have a high sodium chloride content, which can have a disadvantageous effect on the following racemate cleavage. Moreover, the use of HCl and NaOH leads to higher production costs. Moreover, when using alkali metal hydroxides, the pantolactone is generally saponified to the corresponding pantoates. However, racemate cleavage of pantoates is complex and cost-intensive. Consequently, it is advantageous if the product obtained is pantolactone as an enantiomer mixture, which can then be subjected to an enzymatic enantiomer separation.

The object of the present invention is to provide an improved process for the preparation of pantolactone which overcomes as many of the aforementioned disadvantages as possible.

Surprisingly, it has now been found that pantolactone can advantageously be prepared if hydroxypivalaldehyde cyanohydrin is firstly reacted with an adequate molar excess of neutralization equivalents of an acid in a single-phase reaction mixture, and this is then subjected to a neutralization, it being avoided that the reaction mixture obtained after the neutralization has concluded has an excessively high pH and an excessively high water content. Advantageously, during the neutralization the reaction mixture separates into two phases, with the upper organic phase comprising the pantolactone in high concentration, and the lower aqueous phase comprising a highly concentrated, preferably saturated, salt solution.

SUMMARY OF THE INVENTION

The invention provides a process for the preparation of pantolactone (I)

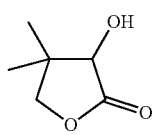

in which
a) an aqueous composition which comprises hydroxypivalaldehyde cyanohydrin (II)

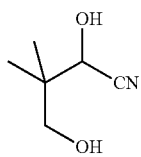

is provided as starting material,
b) the starting material provided in step a) is subjected to a reaction with a strong acid at a pH of less than 1.1 in a homogeneous liquid phase,
c) at least one base is added to the reaction product from step b), with an organic phase being formed which comprises the pantolactone (I), and an aqueous phase which comprises the base salt of the strong acid,
d) the phases are left to separate and the organic phase is separated off from the aqueous phase.

In a specific embodiment of the process according to the invention, the acid used is $H_2SO_4$ and the base used is $NH_3$.

DESCRIPTION OF THE INVENTION

The process according to the invention has the following advantages:
The product can be isolated by the phase separation process according to the invention in the form of an organic phase (upper phase) with a very high pantolactone content. The aqueous phase (lower phase) obtained is a highly concentrated, preferably saturated, salt solution (when using $H_2SO_4$ as acid and $NH_3$ as base, for example, a saturated aqueous ammonium sulfate solution).

The use of external organic solvents, e.g. as extractants, can be dispensed with.

In the process according to the invention, the use of hydrogen chloride and specifically of gaseous HCl for converting the cyanohydrin to the pantolactone can be dispensed with. It is also possible to dispense with the use of alkali metal hydroxides for the neutralization. The process according to the invention thus permits the preparation of pantolactone with a low sodium chloride content.

Using the phase separation process according to the invention it is possible to avoid the saponification of the pantolactone to the pantoate. The pantolactone thus obtained in the form of a D,L-isomer mixture is advantageously suitable for use in an enzymatic enantiomer separation.

To determine the pH values in the process according to the invention, standard commercial pH measurement chains based on a pH electrode and a reference electrode, for example in the form of a single-rod measurement chain, can be used. Unless stated otherwise below, the pHs are temperature-compensated. For the compensation, for example, a pH measurement chain can be used which has a temperature sensor, e.g. a resistance thermometer. Measurement chains of this type ascertain the temperature at the measurement site and pass this on to the measurement device so that the temperature correction takes place automatically. If the measurement solution is subject to only slight temperature fluctuations, or none at all, it is also possible to ascertain the temperature separately once or at adequate time intervals and to manually enter the value ascertained in this way into the measuring device, which then undertakes the pH correction on the basis of these temperature data. The pH determination in the two-phase reaction mixture in step c) preferably takes place in the thoroughly mixed emulsion. It has been found that the measurement values ascertained in this way correspond to the values ascertained after a phase separation in the aqueous phase.

In the context of the invention, a reaction system is referred to as being homogeneous if it consists of a single phase, and as being heterogeneous if it is made up of two or more phases. A reaction in a homogeneous liquid phase is synonymous with a single-phase reaction in liquid phase.

Unless specified in more detail below, "pantolactone" and the formula (I) refers to both the enantiomers in pure form as well as to racemic and optically active mixtures of the enantiomers of the pantolactone. Merely for the purposes of illustration, D-pantolactone and L-pantolactone are given below:

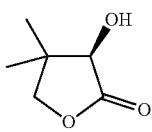 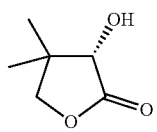

D-pantolactone         L-pantolactone

The terms "hydroxypivalaldehyde" and "hydroxypivalinaldehyde" are used synonymously.
Step a)
In step a) of the process according to the invention, an aqueous composition is provided which comprises hydroxypivalaldehyde cyanhydrin (II). The provision can take place by processes known to the person skilled in the art.

Preferably, to provide the starting material in step a):
a1) formaldehyde is subjected with isobutyraldehyde to an aldol addition, giving hydroxypivalaldehyde, and
a2) the hydroxypivalaldehyde is reacted with a cyanide source, giving hydroxypivalaldehyde cyanhydrin (II).

Such a process is known to the person skilled in the art and described for example in DE-A-27 58 883, to which reference is made here.

Formaldehyde and isobutyraldehyde are available on an industrial scale.

The reaction in step a1) preferably takes place at a temperature of from 20 to 105° C., preferably from 40 to 95° C.

The reaction in step a1) can in principle be carried out at subatmospheric pressure, atmospheric pressure or superatmospheric pressure.

The aldehydes can be used in a stochiometric amount or any of the aldehydes can be used in excess. Preferably, the formaldehyde is used in an amount of from 0.9 to 1.5 mol, in particular 0.9 to 1.1 mol, per mole of isobutyraldehyde.

In a specific embodiment, the reaction mixture from step a1) is used in step a2) without work-up.

In step a2), the cyanide source used is preferably hydrocyanic acid (HCN). The hydrocyanic acid can be used as a gas or expediently in the form of an aqueous solution.

The reaction in step a2) preferably takes place at a temperature of from 10 to 60° C., particularly preferably from 15 to 50° C.

The reaction in step a2) can in principle be carried out at subatmospheric pressure, atmospheric pressure or superatmospheric pressure. Preferably, the reaction is carried out under ambient pressure.

Step b)

Preferably, $H_2SO_4$ is used as acid in step b).

In a specific embodiment, the acid used in step b) is at least 90% strength $H_2SO_4$. Of suitability is, for example, a 96% strength $H_2SO_4$, as is available industrially.

Preferably, in step b), the molar ratio of the acid used to hydroxypivalaldehyde cyanhydrin (II) is in a range from 0.5:1 to 2:1, preferably 0.7:1 to 1.5:1.

In a specific embodiment, in step b), the hydroxypivalaldehyde cyanhydrin-containing starting material is subjected to a reaction with 0.9 to 1.2 mol equivalents of $H_2SO_4$, preferably 1.05 to 1.10 mol equivalents of $H_2SO_4$, based on hydroxypivalaldehyde cyanhydrin.

Preferably, during the reaction in step b), the pH of the reaction mixture is kept in a range from 0 to 1.2, preferably from 0.2 to 1.

Preferably, a single-phase reaction mixture is present during the reaction in step b).

Preferably, the reaction in step b) takes place at a temperature from 50 to 110° C., particularly preferably from 60 to 105° C., in particular from 75 to 100° C.

In a first preferred embodiment, the reaction in step b) takes place at a pressure in the range from 850 to 1150 mbar, preferably from 900 to 1100 mbar. This normal pressure variant is advantageous since it is possible to dispense with complex devices for operating under reduced or elevated pressure. It can be used specifically if no volatile components, such as e.g. water, are to be removed from the reaction mixture during the reaction in step b).

In a second preferred embodiment, the reaction in step b) takes place at a pressure in the range from 100 to 800 mbar, preferably from 200 to 700 mbar. This low-pressure variant is used specifically if volatile components, specifically water, are to be removed from the reaction mixture during the reaction in step b). Accordingly, in a preferred embodiment of the invention, water is removed distillatively from the reaction mixture during the reaction in step b). This makes it possible to use aqueous bases during the neutralization in subsequent step c) without undesirably increasing the water content in the process. Consequently, the aim that the aqueous phase obtained in step c) comprises the base salt of the strong acid in as concentrated a form as possible is achieved. When using $NH_3$ as base, it is therefore for example possible to use aqueous ammonia instead of $NH_3$ gas, which results in a lower heat of reaction.

In a specific variant of the second preferred embodiment described above, the reaction in step b) takes place at a pressure in the range from 100 to 800 mbar, preferably from 200 to 700 mbar, and water is removed distillatively from the reaction mixture during the reaction in step b), and aqueous ammonia is added as base in step c) to the reaction product from step b).

The reaction is step b) can take place in the presence of an inert gas, such as nitrogen, neon or argon.

The reaction in step b) can be carried out discontinuously or continuously. Preferably the reaction in step b) is carried out continuously.

Suitable reactors for the reaction in step b) are in principle reactors which are suitable for carrying out chemical reactions in liquid phase. For the reaction in step b), it is possible to use one reactor or several identical or different reactors. In the simplest case, the reaction in step b) takes place in an individual reactor. If two or more reactors are used, then these can in each case have identical or different mixing characteristics.

The individual reactors can, if desired, be subdivided one or more times by means of internals. If two or more than two (e.g. 3, 4 or 5) reactors are used, then these can be connected as desired with one another, e.g. in parallel or one behind the other (in series). In a preferred embodiment, an individual reactor or a cascade of at least two serially connected reactors is used.

Suitable reactors are e.g. tubular reactors, which can optionally be provided with internals, stirred-tank reactors, loop reactors, etc. Suitable loop reactors are e.g. free-jet reactors, jet-loop reactors, jet-nozzle reactors, etc. To commix the reactors, customary mixing devices can be used. These include e.g. static or dynamic mixers, devices for pumping the reaction mixture and combinations thereof. Preference is given to using at least one mixing device, which is selected from stirrers, mixing nozzles, mixing pumps, static mixing elements, packed beds, etc. Suitable stirrer types comprise e.g. paddle stirrers, anchor stirrers, inclined-blade stirrers, beam stirrers, helical stirrers, screw stirrers, propeller stirrers, impeller stirrers, disk stirrers, turbine stirrers, etc.

The reactors can be equipped with customary devices for introducing or dissipating heat. Suitable heat exchangers are the customary devices known to the person skilled in the art in which heat is transferred from one medium to another, such as e.g. tube-coil heat exchangers, plate heat exchangers, ring groove heat exchangers, finned tube heat exchangers, lamella heat exchangers, double-tube heat exchangers, shell-and-tube heat exchangers, split tube heat exchangers, disk heat exchangers, candle heat exchangers, spiral heat exchangers, block heat exchangers, screw heat exchangers and helical heat exchangers.

For the reaction in step b), an individual stirred-tank reactor or a stirred-tank reactor cascade of two or three stirred-tank reactors is preferably used.

The reactors used for the reaction in step b) can have a device for introducing an inert gas. The introduction of inert gases here can take place into the liquid phase present in the reactor or into the gas phase.

In the simplest case, the reaction in step b) takes place in batch mode in an individual reactor, preferably a stirred-tank reactor. Then, for example, an aqueous solution of the cyanohydrin can be introduced as initial charge in the reactor and the strong acid added. Preferably, the acid addition takes place with good commixing of the reaction mixture. On account of the heat of dilution, a heating of the reaction mixture takes place simply as a result of the addition of acid. Additionally, the liquid reactor contents are heated in order to reach the reaction temperature desired for the conversion. Heating can generally be started if the reactor contains an adequate amount of liquid which permits commixing of the reactor contents. If the reaction in step b) is carried out in batch mode, then the reaction time is preferably in a range from 30 minutes to 600 minutes, preferably 45 minutes to 300 minutes, in particular 60 minutes to 240 minutes, such as e.g. 120 minutes. The reaction time is understood here as meaning the time from which the reaction mixture is heated for the first time at the minimum reaction temperature until the conclusion of the reaction.

The reaction in step b) is preferably carried out continuously. Then, the reaction can take place in an individual reactor or in a reaction system of several reactors. In a specific embodiment of the process according to the invention, the reaction in step b) takes place in a plurality (e.g. two, three, four or more than four) reactors. These are preferably all connected in series. Preferably, the reaction takes place in two or three, in particular in two, serially connected reactors. The first reactor used is preferably a stirred reactor which has two separate feeds for the hydroxypivalaldehyde cyanohydrin-containing starting material and the strong acid. If desired, further feeds can be present, e.g. in order to add water or other solvents to the reaction mixture. However, such an addition of water or other solvents is generally not required. To initiate the reaction, the first reactor can be charged in parallel with the hydroxypivalaldehyde cyanohydrin-containing starting material and the strong acid. Preferably, the initiation takes place with good commixing of the reaction mixture. For this purpose, it may be useful to charge the first reactor firstly with a minimum amount of the hydroxypivalaldehyde cyanohydrin-containing starting material until commixing of the reactor contents is possible, and only then to start introducing the strong acid. In the case of the continuous procedure of the reaction in step b), the heating of the reaction mixture is generally started at the earliest when the reactor comprises an adequate amount of liquid which permits commixing of the reactor contents. After achieving the steady state, the reaction mixture preferably has an average residence time in the first reactor in the range from 10 minutes to 300 minutes, preferably 20 minutes to 200 minutes, in particular 30 minutes to 150 minutes.

The second reactor (and optionally further reactors) should serve to complete the reaction through further conversion of the reaction mixture for an adequate residence time. Suitable reactors for this reaction stage are, for example, stirred-tank reactors or tubular reactors. To ensure an adequate residence time, the second reactor (and if present further reactors) can be filled e.g. partly or completely with a packing and/or have a stream circulated externally (external circulation stream, liquid circulation). Specific residence time packings which allow the required reaction time to be observed are known to the person skilled in the art. In a specific embodiment, the second reactor has a stream circulated externally. After achieving the steady state, the reaction mixture preferably has an average residence time in the second reactor in the range from 10 minutes to 300 minutes, preferably 20 minutes to 200 minutes, in particular 30 minutes to 150 minutes.

If the reaction in step b) is carried out continuously in a reaction system of a plurality of reactors, then the temperature in all of the reactors is preferably in a range from 50 to 110° C., particularly preferably from 60 to 105° C., in particular from 75 to 100° C. If the reaction system comprises more than one reactor, then these may have identical or different temperatures. Equally, one reactor can have a plurality of reaction zones which are operated at different temperatures. Thus, for example, a higher temperature can be established in a second reaction zone of an individual reactor than in the first reaction zone, or a higher temperature can be established in the second reactor of a reactor cascade than in the first reactor, e.g. in order to achieve as complete a conversion as possible.

As stated previously, the reaction in step b) takes place in a first preferred embodiment at a pressure in the range from 850 to 1150 mbar, preferably from 900 to 1100 mbar. In a second preferred embodiment, the reaction in step b) takes place at a pressure in the range from 100 to 800 mbar, preferably from 200 to 700 mbar. These values are in principle independent of whether the reaction in step b) is carried out discontinuously or continuously. These values are also in principle independent of whether the reaction in step b) is carried out in one reactor or in a plurality of reactors. When using a plurality of reactors, the reaction pressure can be the same in all reactors or different in individual reactors.

In a preferred embodiment of the low-pressure variant described above, water is removed distillatively from the reaction mixture during the reaction in step b). This distillative removal of water can in principle take place by customary processes known to the person skilled in the art. In a suitable embodiment, a water-containing gas is distilled off during the reaction, the vapor is at least partially condensed, and the condensate is separated off. All suitable condensers can be used for the condensation or partial condensation of the vapor. These can be cooled using any desired cooling media. Of suitability are, for example, condensers with air cooling and/or water cooling. The heat of condensation of the vapor can be utilized in the process according to the invention or in another process.

If the reaction in step b) is carried out in a plurality of reactors, then the distillative removal of water can take place only from one reactor or from several of the reactors. In a specific embodiment, the reaction in step b) is carried out in a plurality of reactors, and the distillative removal of water takes place at least from the first reactor in the direction of flow of the reaction mixture. More specifically, the distillative removal of water takes place only from the first reactor in the direction of flow of the reaction mixture.

Step c)

In step c) of the process according to the invention, at least one base is added to the reaction product from step b), wherein an organic phase is formed which comprises the pantolactone (I), and an aqueous phase which comprises the base salt of the strong acid.

In a preferred embodiment of the process according to the invention, in step c), at least one base is added to the reaction product from step b) until the pH is in a range from 3 to 7, preferably from 4 to 6, in particular from 4.5 to 5.5. A particularly preferred pH is about 5.

The pH can be determined by the procedure described at the start. The stated pHs are temperature-compensated and refer to 20° C. The pH determination in step c) preferably takes place in the thoroughly mixed emulsion. It has been found that the measurement values determined in this way correspond to the values determined after a phase separation in the aqueous phase.

Preferably, the base used in step c) is selected from $NH_3$, NaOH and KOH. Particularly preferably, $NH_3$ is used in gaseous or in aqueous form.

If $NH_3$ in aqueous form is used as base in step c), then the mass fraction of $NH_3$ is preferably in a range from 15 to 30%. Of suitability is e.g. an industrially available 25% strength ammonia solution (concentration 13.30 mol/l).

As stated previously, it may be advantageous when using aqueous bases in step c) to distillatively remove water from the reaction mixture beforehand during the reaction in step b).

Preferably, the water content of the reaction mixture in step c) after the addition of the base is in a range from 40 to 60% by weight, preferably from 45 to 50% by weight, based on the total weight of the reaction mixture.

Step d)

The two-phase product obtained in step c) is subjected to a phase separation in step d).

In the simplest case, the reaction in step c) takes place in batch mode. Then, the phase separation can be carried out after the addition of base has been concluded in the same reactor which is used for the reaction in step c).

In a preferred embodiment of the process according to the invention, the two-phase product obtained in step c) is subjected to a phase separation in a separate phase separation device in step d).

Suitable phase separation devices and processes for phase separation (liquid-liquid separation) are described for example in Ullmann's Encyclopedia of Industrial Chemistry, sixth edition, 2000 electronic release, chapter "Liquid-Liquid Extraction", there particularly in subchapter 4 "Phase-Separation Equipment". Preferred phase separation devices are phase separators, decanters, centrifuges, coalescers, mixer settler apparatuses and combinations thereof. In particular, the phase separation in step d) takes place using at least one phase separation container (sedimentation container).

Preferably, in step d), the phases are left to separate at a temperature in the range from 50 to 100° C., particularly preferably from 60 to 98° C., in particular from 70 to 95° C. For this purpose, preferably at least one heatable phase separation device is used. On account of the better solubility of the base salts of the strong acid (e.g. of ammonium sulfate) in water, it is advantageous to carry out the phase separation at elevated temperature in order to utilize the salting-out effect as optimally as possible. Consequently, the fraction of pantolactone in the aqueous phase can be minimized.

In a specific embodiment, heat-insulated or heated lines are used for transferring the two-phase product obtained in step c) to a phase separation device. As a result, an undesired precipitation of the base salt of the strong acid (e.g. ammonium sulfate) can be effectively avoided.

The phase separation device used in step d) can be effected by means of a device for introducing an inert gas. In this connection, it generally suffices to feed at least one inert gas into the gas space above the liquid phases and to channel a waste-gas stream out of the gas space at another point.

Preferably, the organic phase obtained in step d) has a content of pantolactone (I) of at least 65% by weight, particularly preferably of at least 70% by weight, in particular of at least 72% by weight, specifically of at least 75% by weight, based on the total weight of the organic phase.

Preferably, the organic phase obtained in step d) has a content of water of at most 25% by weight, particularly preferably of at most 20% by weight, in particular of at most 18% by weight, specifically of at most 17% by weight, based on the total weight of the organic phase.

Preferably, the organic phase obtained in step d) essentially has no saponification products of the pantolactone (pantoates). Preferably, the organic phase obtained in step d) has a content of pantoates of at most 1% by weight, particularly preferably of at most 0.5% by weight, in particular of at most 0.1% by weight, specifically of at most 0.05% by weight, based on the total weight of the organic phase.

Preferably, the aqueous phase obtained in step d) has a content of pantolactone (I) of at most 5% by weight, particularly preferably of at most 4% by weight, in particular of at most 3% by weight, specifically of at most 2% by weight, based on the total weight of the aqueous phase.

Preferably, the aqueous phase obtained in step d) has a content of the base salt of the strong acid of at least 35% by weight, particularly preferably of at least 40% by weight, in particular of at least 43% by weight, specifically of at least 45% by weight, based on the total weight of the aqueous phase.

For example, when using sulfuric acid as strong acid and ammonia as base according to the process of the invention, an optimum enrichment of D,L-pantolactone in the organic phase of about 75% by weight will be attained at a pH around 5. Concurring with this, the residual pantolactone content in the water phase drops as a result of the salting-out effect of the resulting ammonium sulfate to about 1.95% by weight.

Step e)

A specific embodiment of the invention relates to a process in which, additionally, e) the organic phase which comprises the pantolactone (I) is subjected to a work-up.

For the work-up, the organic phase can be subjected to at least one work-up step. These are generally work-up methods customary in the art. The work-up in step e) preferably takes place by distillation, washing, drying, filtration, stripping or a combination of at least two of these measures. The work-up steps can in each case be performed once or several times.

For the washing, the organic phase which comprises the pantolactone (I) is brought into contact in at least one washing apparatus with an aqueous washing medium. Suitable washing media are water and aqueous salt solutions. Preferred washing media are saturated aqueous solutions of the salt from the strong acid used in step b) and the base used in step c). Consequently, as a rule, e.g. the water content of the organic phase can be further reduced. The washing can be carried out for example in a stirred container or in other conventional apparatuses, e.g. in a column or mixer settler apparatus.

A filtration can for example be useful in order to remove precipitated solids, e.g. salts.

Preferably, the organic phase in step e) is subjected to a distillative separation, giving at least one fraction enriched in pantolactone (I) and at least one fraction depleted in pantolactone (I).

For the distillation it is in principle possible to use any distillation column. The distillation can be carried out in one or more stages. Suitable devices for the distillative work-up comprise distillation columns, such as tray columns which can be provided with bubble caps, sieve plates, sieve trays, packings, internals, valves, side take-offs, etc. Also of suitability are dividing wall columns which can be provided with side take-offs, return circuits, etc. A combination of two or more than two distillation columns can be used for the distillation. Also of suitability are evaporators, such as thin film evaporators, specifically falling film evaporators, thin film evaporators with rotating wipers, specifically Sambay evaporators, etc. and combinations thereof.

The process according to the invention gives rise to a D,L-enantiomer mixture of pantolactone which is advantageously suitable for use for racemate cleavage. In this connection, it is possible to use e.g. directly the organic phase from step d) or a product obtained therefrom after work-up. In a specific embodiment, a pantolactone-enriched fraction from step e) according to the invention is used for the racemate cleavage.

The racemate cleavage can take place by customary processes known to the person skilled in the art. Thus, e.g. EP 0443406 A2 describes the preparation of (R)-(-)-pantolactone by cleavage of racemic pantolactone. In the process, racemic pantolactone is subjected, in the presence of lipase from *Pseudomonas* or porcine pancreas, to an enantioselective esterification with certain vinyl esters or methyl vinyl esters, wherein optically active (R)-(-)-pantolactone is left behind and separated from the pantolactone ester formed.

WO 0132890 describes L-pantolactone hydrolase and a process for the preparation of D-pantolactone.

As regards the racemate cleavage, reference is made to the teaching of the cited documents in its entirety.

DESCRIPTION OF THE FIGURES

The process according to the invention is explained in more detail below by means of FIG. 1, without limiting it to this embodiment.

In FIG. 1 the following abbreviations and reference signs are used:
HPACH aqueous hydroxypivalinaldehyde cyanohydrin solution
A acid, 98% $H_2SO_4$ for example
B base, $NH_3$ for example
$N_2$ inert gas stream, in particular nitrogen
G exhaust gas
W aqueous phase, lower phase
PLtech organic phase with pantolactone
R1 reactor
R2 residence time vessel
R3 neutralization vessel
R4 phase separation vessel FIG. 1 shows, schematically, equipment for carrying out the process according to the invention continuously. Aqueous hydroxypivalinaldehyde cyanohydrin solution (HPACH) and sulfuric acid (A) are metered in to a reactor R1 in parallel, i.e. simultaneously via separate lines, for example via pumps. The reaction in the reactor R1 takes place under inert gas atmosphere ($N_2$) homogeneously in liquid phase. The single-phase reaction mixture arrives, after the desired residence time, for example, via an overflow at the heated, horizontal residence time container R2. For the purposes of better mixing of its contents, the reactor R2 is provided with an external circuit. With adequate residence time for complete conversion, the reaction batch flows into the stirred neutralization container R3. In reactor R3, the pH is recorded continuously or at certain intervals. The desired pH is established through metered addition of gaseous ammonia with simultaneous cooling. The resulting emulsion is passed to phase separation container R4. There, an organic upper phase which comprises the pantolactone (Pltech), and an aqueous lower phase (aqueous phase) are formed. The two phases are removed separately. The organic phase comprising the product can be fed to a further work-up. The aqueous lower phase can be recycled to the process optionally after an intermediate purification or can be discharged from the process.

The examples below serve to illustrate the invention without limiting it in any way.

EXAMPLES

Example 1

Reaction of Hydroxypivalinaldehyde Cyanohydrin (HAPACH) with Concentrated Sulfuric Acid and Gaseous Ammonia in Semibatch Mode at Atmospheric Pressure to Give D,L-Pantolactone Starting at approx. 80° C., 962.8 g of HAPACH solution and 303.4 g of 96% strength sulfuric acid are metered in in parallel, with stirring and nitrogen blanketing, over the course of 0.5 h into an initial charge of a mixture of 132.3 g of an approx. 38% strength aqueous hydroxypivalinaldehyde cyanohydrin solution and 41.6 g of 96% strength sulfuric acid. When the metered addition is complete, the single-phase reaction mixture (pH=0.3) is after-stirred for 2 h at 100° C. and then cooled to 70° C. Upon the addition of 62.5 g of gaseous ammonia via immersion tube to a pH of 5.0, the formation of two phases takes place.

Phase separation at 80° C. produces 545.0 g of organic upper phase with a content of D,L-pantolactone of 75.1% by weight (HPLC) and 948.2 g of aqueous lower phase with a D,L-pantolactone fraction of 1.47% by weight (HPLC).

Example 2

Reaction of Hydroxypivalinaldehyde Cyanohydrin (HAPACH) with Concentrated Sulfuric Acid and 25% Strength Aqueous Ammonia in Batch Mode in Vacuo to Give D,L-Pantolactone Initially introduce 972.5 g of an approx. 38% strength aqueous hydroxypivalinaldehyde cyanohydrin solution and, at a pressure of 570 to 580 mbar abs. and a temperature of 80 to 85° C., meter in 307.8 g of 96% strength sulfuric acid over the course of 45 minutes. The temperature increases to about 90° C. and around 177.4 g of water and low boilers distil off. After the metered addition of sulfuric acid is complete, the single-phase reaction mixture is after-stirred for 2 h at 100° C. and the vacuum is then lifted by aerating with nitrogen. Addition of 233.4 g of 25% strength aqueous ammonia to pH 5.0 leads to the formation of two phases.

Organic upper phase: 467.4 g with a D,L-pantolactone fraction of 75.7% by weight (HPLC)

Aqueous lower phase: 850.6 g with a D,L-pantolactone content of 1.36% by weight (HPLC)

Example 3

Reaction of Hydroxypivalinaldehyde Cyanohydrin (HAPACH) with Concentrated Sulfuric Acid and Gaseous Ammonia in Continuous Mode at Atmospheric Pressure to Give D,L-Pantolactone For the reaction, equipment according to FIG. 1 is used. Under blanketing with nitrogen and stirring at 94 to 96° C., approx. 36% strength aqueous hydroxypivalaldehyde cyanohydrin solution (HAPACH) is metered into the reactor R 330 at a rate of 835.5 g/h, and 96% strength aqueous sulfuric acid is metered in in parallel at a rate of 250.0 g/h via pumps from weighed initial charges.

After a residence time of approx. 80 minutes, the single-phase reaction mixture passes via a free overflow into the horizontal residence time container B 331, which is likewise heated to 94 to 96° C. and whose contents are pumped using an external circuit for better mixing with a 6-fold volume change per hour. After a residence time of approx. 80 minutes, the completely reacted reaction batch then flows into the stirred neutralization container R 643. As a result of the metered addition of gaseous ammonia at a rate of 46 g/h, a pH of 5.0 is established with simultaneous cooling to 79 to 80° C. In the subsequent container B 732, at 80° C., 379.1 g/h of organic upper phase with a weight fraction of 75.5% of D,L-pantolactone (determined by means of HPLC) separate off from the resulting emulsion. The aqueous lower phase, following its removal in the run-off, is also diluted with approx. 235 g/h of completely demineralized water in order to avoid crystallizate formation due to ammonium sulfate. The diluted aqueous solution (total amount 986.8 g/h) comprises a further 1.35% by weight of D,L-pantolactone (determined by means of HPLC).

Example 4

Reaction of Hydroxypivalinaldehyde Cyanohydrin (HAPACH) with Concentrated Sulfuric Acid and 25% Strength Aqueous Ammonia in Continuous Mode in Vacuo to Give D,L-Pantolactone To carry out the reaction at reduced pressure using the equipment according to FIG. 1, the following changes are made:

1.) Replacement of the reflux condenser on the reactor R 330 with a column head with distillation receiver.
2.) Connection of the reactor R 330 to an external vacuum (approx. 580 mbar) instead of the nitrogen blanketing.
3.) Replacement of the free overflow between R 330 and B 331 with a pump with fill level regulation which ensures the transfer of the reactor contents from the subatmospheric pressure range of reactor R 330 to the subsequent apparatuses which are operated at atmospheric pressure.
4.) Use of 25% strength aqueous ammonia solution for neutralization, which is conveyed from a weighed initial charge by means of a pump to the neutralization container R 643.

With stirring at 94 to 96° C., approx. 38% strength aqueous hydroxypivalinaldehyde cyanohydrin solution (HAPACH) is metered into the reactor R 330, evacuated to 580 mbar, at a rate of 835.5 g/h, and 96% strength aqueous sulfuric acid is metered in in parallel at a rate of 250.0 g/h via pumps from weighed initial charges, with, at the same time, about 127 g of water and low boilers being drawn off per hour via the top of the column into the distillation receiver.

After a residence time of approx. 45 minutes under fill level regulation, the single-phase reaction mixture is conveyed with the help of a pump into the residence time container B 331. The residence time container B 331, held at atmospheric pressure under nitrogen blanketing, is likewise heated to 94 to 96° C. and the contents are pumped around via an external circuit for better mixing with a 6-fold volume exchange per hour.

After a residence time of approx. 90 minutes, the completely converted reaction batch then flows into the stirred neutralization container R 643. As a result of the metered addition of 25% strength aqueous ammonia at a rate of 171.2 g/h, a pH of 5.0 is established with simultaneous cooling to 79 to 80° C. In the subsequent container B 732 at 80° C., 374.6 g/h of organic upper phase with a weight fraction of 76.15% of D,L-pantolactone (determined by means of HPLC) separate off from the resulting emulsion. Following its removal in the run-off, the aqueous lower phase is further diluted with approx. 180 g/h of completely demineralized water in order to avoid crystallizate formation due to ammonia sulfate. The diluted aqueous solution (total amount 936.2 g/h) also comprises a further 1.28% by weight of D,L-pantolactone (determined by means of HPLC).

The invention claimed is:

1. A process for the preparation of pantolactone (I)

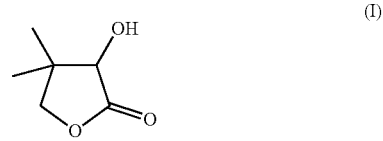

comprising:
a) providing an aqueous composition which comprises hydroxypivalaldehyde cyanohydrin (II)

as starting material,
b) subjecting the starting material provided in step a) to a reaction with $H_2SO_4$ as acid at a pH of less than 1.1 in a homogeneous liquid phase,
c) adding $NH_3$ in gaseous or aqueous form as base to the reaction product from step b) until the pH is in a range from 3 to 7 and where the water content of the reaction mixture in step c) following the addition of the base is in a range from 40 to 60% by weight, based on the total weight of the reaction mixture, with an organic phase being formed which comprises the pantolactone (I), and an aqueous phase which comprises the base salt of the strong acid,
d) leaving the phases to separate and separating off the organic phase from the aqueous phase.

2. The process according to claim 1, where, for the provision of the starting material in step a):
a1) formaldehyde is subjected with isobutyraldehyde to an aldol addition, giving hydroxypivalaldehyde, and
a2) the hydroxypivalaldehyde is reacted with a cyanide source, giving hydroxypivalaldehyde cyanohydrin (II).

3. The process according to claim 1, where the acid used in step b) is at least 90% strength $H_2SO_4$.

4. The process according to claim 1, where, during the reaction in step b), the pH of the reaction mixture is kept in a range from 0 to 1.2.

5. The process according to claim 1, where, in step b), the molar ratio of the acid used to hydroxypivalaldehyde cyanohydrin (II) is in a range from 0.5:1 to 2:1.

6. The process according to claim 1, where the reaction in step b) takes place at a temperature from 50 to 110° C.

7. The process according to claim 1, where the reaction in step b) takes place at a pressure in the range from 850 to 1150 mbar.

8. The process according to claim 1, where the reaction in step b) takes place at a pressure in the range from 100 to 800 mbar.

9. The process according to claim 8, where, during the reaction in step b), water is removed distillatively from the reaction mixture.

10. The process according to claim 1, where, in step c), at least one base is added to the reaction product from step b) until the pH is in a range from 4 to 6.

11. The process according to claim 1, where the reaction in step b) takes place at a pressure in the range from 200 to 700 mbar, and during the reaction in step b) water is removed distillatively from the reaction mixture and, in step c), aqueous $NH_3$ is added as base to the reaction product from step b).

12. The process according to claim 1, where the water content of the reaction mixture in step c) following the addition of the base is in a range from 45 to 50% by weight, based on the total weight of the reaction mixture.

13. The process according to claim 1, where, in step d), the phases are left to separate at a temperature in the range from 50 to 100° C.

14. The process according to claim 1, further comprising
  e) subjecting the organic phase which comprises the pantolactone (I) to a work-up.

15. The process according to claim 14, where the organic phase is subjected to a distillative separation, giving at least one fraction enriched in pantolactone (I) and at least one fraction depleted in pantolactone (I).

16. The process according to claim 14, where the organic phase or at least one fraction enriched in pantolactone (I) is subjected to a racemate cleavage, giving at least one fraction enriched in D-pantolactone.

17. The process according to claim 1, where, during the reaction in step b), the pH of the reaction mixture is kept in a range from 0.2 to 1.

18. The process according to claim 1, where, in step b), the molar ratio of the acid used to hydroxypivalaldehyde cyanohydrin (II) is in a range from 0.7:1 to 1.5:1.

19. The process according to claim 1, where the reaction in step b) takes place at a temperature from 75 to 100° C.

20. The process according to claim 1, where the reaction in step b) takes place at a pressure in the range from 900 to 1100 mbar.

* * * * *